(12) United States Patent
Kühne et al.

(10) Patent No.: US 12,115,130 B2
(45) Date of Patent: Oct. 15, 2024

(54) TABLET HAVING A TWO-DIMENSIONAL IDENTIFIER

(71) Applicants: Laxxon Medical AG, Stetten (CH); Exentis Knowledge GmbH, Stetten (CH)

(72) Inventors: Klaus Kühne, Berlin (DE); Helmut Kerschbaumer, Zürich (CH); Daniel Moldenhauer, Jena (DE); Alexander Ruckdäschel, Raleigh, NC (US); Achim Schneeberger, Vienna (AT)

(73) Assignees: Laxxon Medical AG, Stetten (CH); Exentis Knowledge GmbH, Stetten (CH)

( * ) Notice: Subject to any disclaimer, the term of this patent is extended or adjusted under 35 U.S.C. 154(b) by 202 days.

(21) Appl. No.: 17/702,435

(22) Filed: Mar. 23, 2022

(65) Prior Publication Data

US 2022/0304895 A1   Sep. 29, 2022

(30) Foreign Application Priority Data

Mar. 24, 2021   (DE) ..................... 10 2021 202 880.2

(51) Int. Cl.
*A61J 3/00* (2006.01)
*A61K 9/20* (2006.01)

(52) U.S. Cl.
CPC ............. *A61J 3/007* (2013.01); *A61K 9/2072* (2013.01); *A61J 2205/30* (2013.01)

(58) Field of Classification Search
CPC ...... A61J 3/007; A61J 2205/30; A61K 9/2072
See application file for complete search history.

(56) References Cited

U.S. PATENT DOCUMENTS

2004/0219109 A1   11/2004   Hatch
2013/0088555 A1*   4/2013   Hanina ................... B41J 3/407
                                                      347/107

FOREIGN PATENT DOCUMENTS

DE        19708674 A1    10/1997
WO     2019/129557 A1     7/2019

OTHER PUBLICATIONS

Fist German Examination Report issued for corresponding German Application No. 10 2021 202 880.2, mailed Dec. 20, 2021.
Vaz, V.M. et al., "3D Printing as a Promising Tool in Personalized Medicine" in AAPS PharmSciTech 22, 49 (2021).
Trenfield, S. et al. "Personalising Drug Products Using 3D Printing" in ONdrugDelivery Magazine, Issue 99 (Aug. 2019), pp. 28-32.
Moldenhauer et al., "3D Screen printing—an innovative technology for large-scale manufacturing of pharmaceutical dosage forms" in International Journal of Pharmaceutics (Nov. 2020).
M. Edinger et al., "QR encoded smart oral dosage forms by inkjet printing" in Int. J. Pharm., 2018, 536, 138).

(Continued)

*Primary Examiner* — Jamara A Franklin
(74) *Attorney, Agent, or Firm* — Renner, Otto, Boisselle & Sklar, LLP

(57) ABSTRACT

A solid dosage form for active ingredient release can be a preparation for medical, dental or cosmetic purposes, and is preferably a tablet. The solid dosage form comprises a three-dimensional base body which comprises an active ingredient. The solid dosage form further comprises a portion having a structure forming a two-dimensional identifier, such as, for instance, a QR code.

20 Claims, 3 Drawing Sheets

(56) References Cited

OTHER PUBLICATIONS

Figure 1:
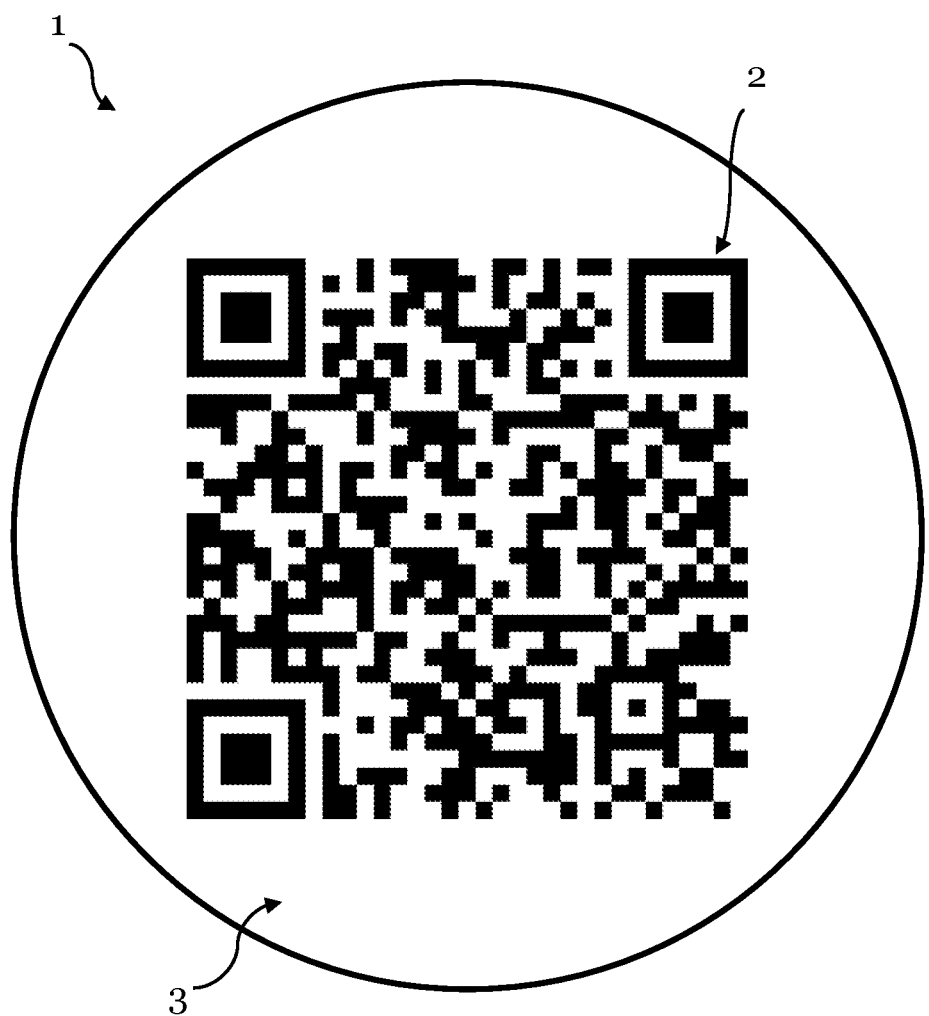

B.-C. Oh et al., "Preparation and evaluation of identifiable quick response (QR)-coded orodispersible films using 3D printer with directly feeding nozzle" in Int. J. Pharm., 2020, 584, 119405.

F. Schneider et al., "In Vitro and in Vivo Test Methods for the Evaluation of Grastroretentive Dosage Forms," Pharmaceutics Nov. 2019, 416.

* cited by examiner

TABLET HAVING A TWO-DIMENSIONAL IDENTIFIER

This application claims priority of German Patent Application No. 10 2021 202 880.2 filed Mar. 24, 2021, the entire disclosure of which is hereby incorporated by reference.

1. TECHNICAL FIELD

The invention relates to a solid dosage form as well as to a method for production of such a dosage form by means of screen printing.

2. TECHNICAL BACKGROUND

Tablets are a frequent dosage form of medicaments, and are used as a medicament form to deliver a pharmaceutical active ingredient to a patient (human or animal). Usually tablets are produced in tablet presses by pressing the starting material, for instance in the form of powder, granules or substrates, under high pressure. In a further step, tablets can be dragged or coated with a coating.

The patient receives important information, in particular concerning the purpose and the correct use of the medicament, from the packaging or the package leaflet. However, there is the problem that a tablet once removed from the packaging can no longer be unambiguously assigned to the respective packaging and the associated package leaflet, since the tablet per se usually cannot be unambiguously identified. There is thus a need for a possibility of an unambiguous authentication of tablets by a patient.

It is known to punch tablets locally in order to indicate few information such as the tablet dose (e.g. "200 mg") on the tablet itself. The rather rough punching in does not allow more extensive information to be indicated, let alone to allow an unambiguous identification or authentication of the tablet. In addition, there is the disadvantage here that in production a tablet is present as an intermediate product into which no information has yet been punched, whereby the medicament safety is impaired. This is because in this stage the unambiguous assignment of the intermediate product is jeopardised, since the intermediate product per se cannot be recognised which product is which batch.

It is known from the prior art to provide QR codes. For example, in the scientific article "QR encoded smart oral dosage forms by inkjet printing" by M. Edinger et al. (Int. J. Pharm., 2018, 536, 138) it is described that by means of inkjet printing a QR code pattern can be printed onto a porous and flexible substrate, wherein the pattern contains the medicament. With a smartphone a patient can scan the QR code and then retrieve the information linked to the QR code.

A similar process is described in the scientific article "Preparation and evaluation of identifiable quick response (QR)-coded orodispersible films using 3D printer with directly feeding nozzle" by B.-C. Oh et al. (Int. J. Pharm., 2020, 584, 119405). There a QR code is printed onto a film by means of a 3D printer.

The above-described methods have the disadvantage that several processes are necessary in order to produce the medicament form. First a suitable substrate has to be produced, and then the QR code has to be printed on in a second process. In addition, the QR code produced by means of inkjet printing or 3D printing can easily be damaged or manipulated.

It is therefore an object of the present invention to at least partially reduce the present disadvantages. In particular, an improved tablet having a QR code or similar identifier is to be provided, which can be produced with little additional effort. In particular, a tablet is to be provided, which can be authenticated by a patient and is distinguished by a high drug safety.

This object is at least partially achieved by a dosage form according to claim 1 as well as by a method according to claim 20.

3. CONTENT OF THE INVENTION

One aspect of the invention relates to a solid dosage form. Such a dosage form can be a preparation for medical, dental or cosmetic purposes, and can be designed, for example, as a tablet, pill or pastille. The dosage form can be a finished preparation which is administered to the patient, for example by peroral, buccal, rectal or vaginal application. The solid dosage form can have a solid surface, and thus differ from liquid dosage forms.

The dosage form can be suitable for delivering an active ingredient into a patient in order to achieve a desired effect there. For this purpose, the dosage form can contain one or more active ingredients, such as, for example, drugs, vitamins, minerals, nutraceuticals, etc. The type and amount of the active ingredient are freely selectable. The dosage form can dissolve after being taken up by a patient, for example in the case of oral uptake, in the mouth via the saliva or in the stomach via the gastric juice. For this purpose, the dosage form can comprise a material which is correspondingly soluble in body fluids. For example, the dosage form can be chewed on uptake. Other areas of application are equally provided. Thus, the solid dosage form can, for example, be dissolved in a glass of water, and subsequently be drunk by the patient in dissolved form.

The dosage form comprises a three-dimensional base body. In this case, the base body can predetermine the form underlying the dosage form. The base body can be solid, and in this case can be substantially dimensionally stable and volume-stable. The base body can be present as a single structural element. In this case, the dosage form can be substantially defined by the base body. The base body can have any desired shape, and for instance have a round outer shape.

In this case, the base body comprises at least one active ingredient, which is to be dispensed by means of the dosage form. For this purpose, the material of the base body or the base body material can contain the active ingredient. In this case, the active ingredient distribution in the base body can be inhomogeneous or heterogeneous, i.e. for instance have a gradient. In this way, constant active ingredient release can be made possible when the dosage form is dissolved. If several active ingredients are provided, these can be arranged locally in the dosage form in such a way that sequential release of the active ingredients is ensured. The dosage form can thus be used for complex administration forms. As a possible active ingredient, drugs, vitamins, minerals, nutraceuticals, etc. can be used. Preferably, the active ingredient is a pharmaceutical active ingredient.

The dosage form further comprises a portion which has a structure forming a two-dimensional identifier. The portion in this case is integral with the base body. The portion thus constitutes a part of the base body, and is not provided separately from the base body. The dosage form is preferably free of applied films or applied elements which comprise a two-dimensional identifier. The portion itself preferably comprises a material which is similar to the material of the base body, so that it blends as homogeneously as possible into the base body. Preferably, the portion comprises the same components or ingredients as the base body, but can comprise still further components or ingredients. The portion can thus be formed from the base body material and further components. The exact composition of the individual components can be variable in this case, for example if the active ingredient is arranged inhomogeneously or heterogeneously in the dosage form. Preferably, the portion is soluble, as described above with regard to the base body. The portion can be regarded as an inherent constituent of the base body. Preferably, the dosage form comprises no further element in addition to the base body and the portion. The portion provided integrally with the base body, the structure of which in turn forms the two-dimensional identifier, in this case itself comprises material, and is therefore distinguished from the previously known "punching in of information". The base body can comprise a first material, and the portion a second material. The first material and the second material can comprise identical contents. The two-dimensional identifier is defined by the structure of the portion. By way of example, the portion can have a specific geometric shape, wherein this geometric shape defines the two-dimensional identifier.

The two-dimensional identifier is preferably visually identifiable from the outside, for instance with the naked eye or by means of a microscope. Alternatively or additionally, the portion can also be haptically identifiable. Preferably, the two-dimensional identifier is readable by means of a camera, in particular a smartphone camera. For this purpose, the portion or the identifier can differ in colour or structure from the rest of the base body in order to form a sufficient contrast.

The two-dimensional identifier can preferably contain and represent information. In particular, the two-dimensional identifier can allow unambiguous authentication of the dosage form. By way of example, an ibuprofen tablet of a specific manufacturer can be identified as such on the basis of the identifier. Preferably, the two-dimensional identifier is associated with information which either inherently emerges from the two-dimensional identifier or is linked thereto. This information can, in addition to the name, the dose and the manufacturer, also describe the purpose and the correct use of the medicament. Preferably, the information can comprise a part or at best all of the data which are conventionally indicated on packaging or package leaflets of medicaments. In one exemplary embodiment, the two-dimensional identifier is linked to information dynamically stored on the Internet, so that a manufacturer can flexibly adapt the information, for instance in order to indicate new side effects. The person skilled in the art understands that any desired suitable information can be displayed to the patient in this way. In particular if the dosage form is used as complex administration forms, and contains several active ingredients to be delivered sequentially, it is advantageous to provide extensive information about this system via the two-dimensional identifier.

The dosage form is advantageous since it is inherently provided with a two-dimensional identifier, with which information can be provided to the patient. By providing the identifier as an inherent constituent of the dosage form, the medicament safety is increased, since unambiguous authentication of the dosage form can be made possible by means of the identifier. Since the identifier cannot be removed without damaging or destroying the dosage form, the medicament safety is further increased.

Preferably, the dosage form is produced by means of screen printing, for instance by means of a screen printing method or a screen printing process. The screen printing method is a printing method in which a printing paste can be printed with a doctor blade through a fine-meshed fabric. The mesh openings of the fabric are closed at those locations of the fabric at which no paste is to be printed according to the printed image, for instance in order to form the structure of the portion. Preferably, at least the portion having the structure is produced by means of screen printing. A detailed structure and thus a high-quality two-dimensional identifier can thus be provided. Preferably, the base body is produced by means of screen printing. Preferably, the entire dosage form is produced by means of screen printing, further preferably by means of a single screen printing process, i.e. in a single screen printing process in which a single printing program is carried out in order to produce the dosage form, without an intermediate product having to be removed from the screen printer for production. This has the advantage that a dosage form having the two-dimensional identifier can be produced, without a process change with an intermediate product without an identifier being necessary. In this way, the medicament safety is further increased. In addition, a dosage form can be provided in this way, in which the portion is formed integrally with the base body, since the portion and also the base body have been produced equally by means of the screen printing method. By means of the screen printing method, suitable structures of the portion can also be provided in order to provide a dosage form having a desired two-dimensional identifier for detailed information.

Preferably, the two-dimensional identifier is a barcode or a QR code. A barcode can be an optoelectrically readable writing comprised of different widths, parallel lines and gaps. A QR code can be comprised of a quadrangular or square matrix of different-coloured, for instance white and black, squares. The squares can represent coded data in binary form, and be read out via a suitable reader, such as for instance a smartphone. The invention is not restricted to any specific type and size of such QR codes. Depending on the size of the dosage form and the information to be represented in the identifier, a suitable level for error correction can be selected in order to ensure trouble-free reading of the information. In further embodiments, the two-dimensional identifier can also comprise text, numbers or symbols. The two-dimensional identifier can be linked to information which is retrievable for instance via the Internet. Detailed information can thus be retrieved via the two-dimensional identifier inherent to the dosage form, which information can serve on the one hand to identify or authenticate the dosage form, and can also be relevant to the use.

Preferably, the two-dimensional identifier can be optically detected, for example by means of a reading unit for a barcode. In a preferred exemplary embodiment, the QR code can be read by means of a smartphone camera in order to output the respective information to the patient via the display of the smartphone. In a preferred exemplary embodiment, the patient can direct the camera of his smartphone onto the QR code of the dosage form, and thereupon receives the name, the dosage and the manufacturer of the dosage form communicated via the display, as well as information on the use and indications of possible side effects.

Alternatively or additionally, the two-dimensional identifier can preferably be a haptic code, wherein the information can be coded for instance in the form of braille. For this purpose, the structure of the portion can be such that it forms a specific contour on the surface of the dosage form, which contour can be haptically identified for instance with the fingertip. In this way, patients with restricted visual perception capability can also identify the identifier and identify the dosage form on the basis thereof.

Preferably, the two-dimensional identifier has a resolution of 50 to 500 dpi, more preferably of 60 to 400 dpi, more preferably of 70 to 300 dpi, more preferably of 80 to 200 dpi, more preferably of 90 to 150 dpi, more preferably of 100 to 120 dpi. By means of a sufficiently high resolution, it is possible to provide many items of information about the two-dimensional identifier.

Preferably, the two-dimensional identifier comprises a point or a line with a thickness between 20 µm and 700 µm, more preferably between 30 µm and 600 µm, more preferably between 40 µm and 500 µm, more preferably between 50 µm and 400 µm, more preferably between 60 µm and 300 µm, more preferably between 70 µm and 200 µm, more preferably between 80 µm and 150 µm. The structure of the portion is thus such that it can form points or lines which at least partially have the stated thickness. Sufficient detectability of the two-dimensional identifier is thus ensured, with a still high information content of the identifier. Further points or lines with a deviating thickness can be provided. In addition, further elements, such as for instance circles, can also be provided.

Preferably, (also or only) the portion contains an active ingredient. Preferably, the portion includes an active ingredient which is also provided in the base body. Preferably, each active ingredient which is comprised by the base body can also be included in the portion. In this way, the portion can also contribute to achieving the therapeutic effect. When distributing active ingredients in the dosage form, the portion can advantageously also be taken into account in order to achieve a desired active ingredient distribution and thus a targeted active ingredient release in the patient.

In a preferred exemplary embodiment, the active ingredient distribution runs continuously through the dosage form over the base body and the portion. In the region of the portion in the base body, the active ingredient distribution can thus be free of discontinuities. For example, a gradual course of the active ingredient distribution can run homogeneously over the base body including the portion. The procurement of the portion therefore does not have to impair the active ingredient distribution in the dosage form. In this way, a specific active ingredient distribution and thus an optimal active ingredient release in the patient can be achieved.

Preferably, the portion contains a colouring agent. The colouring agent can comprise a (soluble) dye or an (insoluble) colour pigment. In this way, the portion or the structure thereof and thus the identifier can be optically identified on the basis of the colouring agent. The colouring agent preferably offers a sufficiently high contrast to the rest of the colour of the base body. The dye is preferably a food additive. Preferably, the portion comprises the same components or ingredients as the base body, and additionally also the colouring agent. In a further exemplary embodiment, the portion can comprise a fluorescent colouring agent such as, for instance, a (food) fluorescent dye or a fluorescent colour pigment. In this way, the identifier can be made identifiable only under specific light conditions, which can improve the visual appearance of the dosage form. Furthermore or alternatively, the portion can comprise nano and/or micro particles in order to predefine a desired spectroscopic reading of the identifier.

Preferably, the portion has a thickness of 2 µm to 1000 µm, more preferably of 3 µm to 300 µm, more preferably of 4 µm to 100 µm, more preferably of 5 µm to 50 µm, preferably of 10 µm to 40 µm, more preferably of 20 µm to 30 µm. The thickness can in this case be measured along an axis which is orthogonal to the plane spanned by the two-dimensional identifier. The structure can thus have a three-dimensional extension, wherein the extension of the structure along the first and second dimension forms the two-dimensional identifier, and the structure along the third dimension has the stated thickness. Sufficiently good detectability of the identifier can thus be made possible.

Preferably, the portion is present at the surface of the dosage form. For example, if the two-dimensional identifier is a haptic code, the portion can be present at the surface in order to allow the patient to feel the haptic code. A portion which forms a QR code can also be arranged at the surface of the dosage form. In particular preferably, an outwardly directed surface of the portion is planar with a surface of the base body. In particular preferably, the surface of the dosage form is smooth and stepless in the region of the portion. The surface of the dosage form thus has a planar surface, at least in the region of the portion, without steps between portion and base body. The portion itself is thus not designed as a relief or counter-relief. This increases robustness of the dosage form, since no regions of the portion protrude which could otherwise easily break off.

Preferably, the portion is not present at the surface of the dosage form. The portion can thus be completely enclosed by material of the rest of the base body. In particular preferably, a (minimum) distance of the portion to a surface of the base body is in the range of 2 µm to 1000 µm, further preferably in the range of 3 µm to 300 µm, further preferably in the range of 4 µm to 100 µm, further preferably in the range of 5 µm to 100 µm, preferably in the range of 10 to 80 µm, further preferably in the range of 15 to 60 µm, and further preferably in the range of 20 to 40 µm. For example, the portion forming the two-dimensional identifier can lie parallel to a planar surface of the base body. If such a parallel arrangement is not present, and/or the surface of the base body or of the dosage form is not planar, the stated distance ranges refer to the shortest distance between the portion and the surface. By covering the portion, the drug safety is further increased, since removal of the identifier is not possible in a non-destructive manner. The material of the base body and of the portion is preferably selected in such a way that optical detection of the enclosed portion is possible. By way of example, the portion can comprise a dark colour, and the rest of the base body can have a light colour, such that the two-dimensional identifier is nevertheless identifiable from the outside on account of the stated short distance from the surface.

Preferably, the portion is not designed as a haptically perceptible relief or counter-relief. Thus, in the cross section of the dosage form, the portion is not arranged in a recessed manner in the surface, and is also not protruding from the latter. This increases robustness of the dosage form. In particular preferably, the dosage form is free of a relief or counter-relief and has a completely smooth surface. In this way, a targeted release behaviour can be achieved by uniform dissolution of the dosage form.

Preferably, the section comprises a marker which is detectable after administration of the dosage form. The marker may in this case be a substance which can be detected from outside the patient, even after the patient has taken the dosage form. For example, it can be identified by means of the marker that the dosage form is located in the body of the patient, for instance in his stomach. In this way, it can advantageously be established that, for example, a tablet has also actually been swallowed by the patient, and has not been forgotten (for instance on account of dementia), hidden or disposed of in some other way. Compliance with the therapy can thus be ensured. Particularly preferably, the marker is detectable by means of an imaging method, such as, for instance, by means of scintigraphy, X-ray radiation, magnetic resonance tomography, magnetic moment imaging. For this purpose, the marker may, for example, comprise the radioisotope 99 mTc, or 113 mIn, in order to be detectable by means of scintigraphy. For detection by means of X-ray radiation, the marker can comprise a suitable contrast agent, such as, for instance, barium sulfate. For detection by means of magnetic resonance tomography or magnetic moment imaging, the marker can likewise comprise a suitable contrast agent, such as, for instance, iron oxide. These and further possibilities for detecting a marker are described in the scientific article "In Vitro and in Vivo Test Methods for the Evaluation of Gastroretentive Dosage Forms" by F. Schneider et al., Pharmaceutics 2019, 11, 416, hereby incorporated by reference. The marker is advantageously provided directly in the portion which predefines the structure for the two-dimensional. In this case, the marker can be provided without requiring further steps for production of the dosage form. With the printing of the section, for example, the marker can also be applied. An additional production step in order to provide the dosage form with the marker is thus advantageously not required.

A further aspect of the present invention relates to a method for production of a dosage form according to the above statements. The production is carried out in this case by means of the screen printing method. In this case, the production method comprises providing a first printing paste comprising the active ingredient, and applying the first printing paste by means of a first printing screen. The main body can be printed by means of the first printing paste. Furthermore, the method comprises providing a second printing paste, preferably comprising a colouring agent such as, for instance, a dye or a colour pigment, and applying the second printing paste by means of a second printing screen. As a result, the portion is formed, having the structure forming the two-dimensional identifier. In this case, a pattern of the second printing screen defines the structure of the portion. The portion can thus be printed by means of the second printing paste.

In this way, it is possible to produce the dosage form, comprising the base body and the portion, layer by layer. Base body and portion are printed in the same production method, so that the portion is ultimately present integrally with the base body. The formation of the two-dimensional identifier is thus also integrated in the complete production method, so that additional processes for marking the dosage form are not required. In this case, the application can also be carried out in such a way that a layer is formed from the first and the second printing paste. For example, a QR code can be formed in a layer by means of the second printing paste, and the first printing paste can be applied in the remaining locations of the layer not occupied by the second printing paste. The person skilled in the art understands that further printing pastes and further printing screens can also be used in addition to the stated printing pastes.

A further aspect of the present invention relates to a dosage form produced with the described method.

4. EXEMPLARY EMBODIMENTS

The invention is described in more detail below on the basis of exemplary embodiments with reference to the accompanying figures. In the figures, identical elements are provided with identical reference signs.

Figure 2:
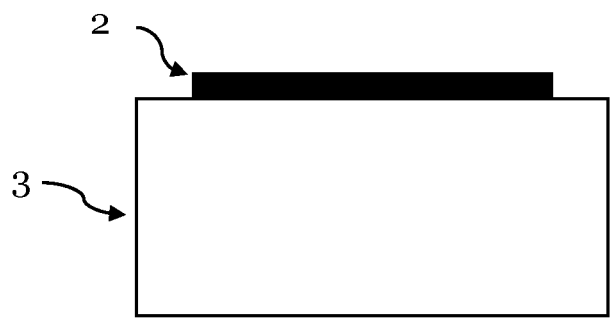
Figure 3:
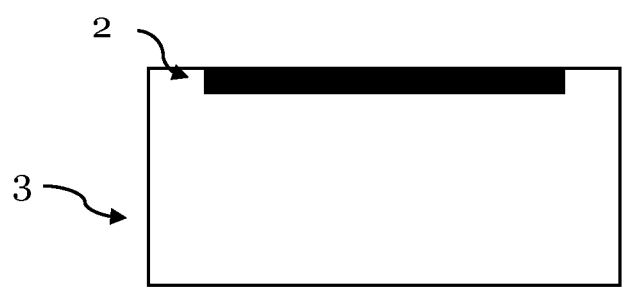
Figure 4:
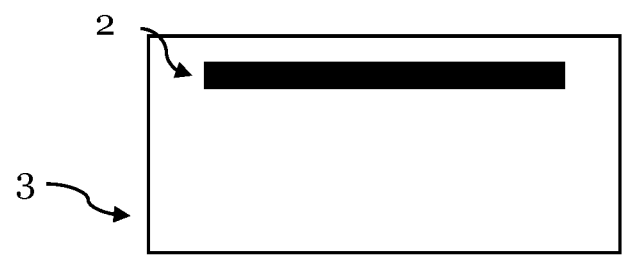
Figure 5:
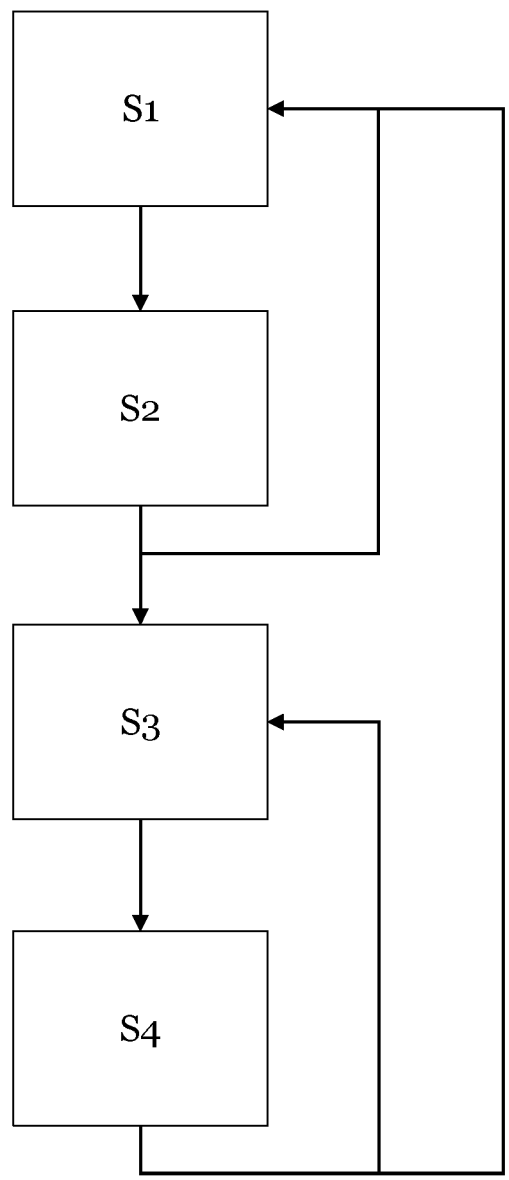

In the figures:

FIG. 1 a tablet having a two-dimensional identifier according to one exemplary embodiment;

FIG. 2 a tablet having a two-dimensional identifier according to a further exemplary embodiment;

FIG. 3 a tablet having a two-dimensional identifier according to a further exemplary embodiment;

FIG. 4 a tablet having a two-dimensional identifier according to a further exemplary embodiment;

FIG. 5 schematically a production method according to a further exemplary embodiment.

FIG. 1 shows a solid dosage form in the form of a tablet 1 according to an exemplary embodiment. The tablet 1 has a round basic shape with an exemplary diameter of 1.5 cm and an exemplary thickness of 0.3 cm. The person skilled in the art understands that the tablet can also have other shapes and sizes.

The tablet comprises a three-dimensional base body 3, which comprises a pharmaceutical active ingredient. Formed integrally with the base body 3 is a portion 2, the structure of which represents a two-dimensional identifier in the form of a QR code. The QR code has an exemplary size of 1×1 cm$^2$ but can also be larger or smaller. A patient can read in the QR code with his smartphone and thereupon receives, for example, the information "acetylsalicylic acid, 500 mg per 1 tablet, chewable tablet". In this way, the person skilled in the art can identify the active ingredient and the dose of the tablet, and receives information concerning the administration form.

FIGS. 2 to 4 each show a cross section through a dosage form according to further embodiments, for example the tablet 1 shown in FIG. 1. Each of these dosage forms can be described analogously to the exemplary embodiment according to FIG. 1, and comprises a base body 3 and a portion 2. In this case, the portion 2 can have a structure which represents, for example, a two-dimensional identifier in the form of a QR code, as shown in FIG. 1. The portion 2 can in this case have an exemplary thickness or thickness of 20 µm, and, as described with reference to FIG. 1, an exemplary size of 1×1 cm$^2$. The embodiments shown in FIGS. 2 to 4 differ in the arrangement of the portion 2.

FIG. 2 shows an embodiment in which the portion 2 is present at the surface of the base body 3. The portion 2 protrudes in this case from the rest of the base body 3. The two-dimensional identifier predefined by the structure of the portion 2 can thus be haptically identified. In a further exemplary embodiment, the identifier can be formed here as a haptic code, for example in the form of braille.

FIG. 3 shows an embodiment in which the portion 2 is likewise present at the surface of the base body 3. In this example, the portion 2 is planar with the surface of the base body 3. Thus, no elements of the portion 2 protrude from the surface, so that no structure can be haptically detected. The identifier in the form of a QR code is optically identifiable and can be detected by means of a camera. The surface of the dosage form is smooth in this case, also in the region of the portion 2. The gaps in the portion 2 at the surface predefined on account of the shape of the QR code are filled in this case by material of the base body 3, so that ultimately no depressions or elevations are identifiable or tactile. The dosage form thus has no relief or counter-relief.

FIG. 4 shows an embodiment in which the portion 2 is not present at the surface of the base body 3. In this example, the portion 2 is completely surrounded by material of the further base body 3. The minimum distance between the portion 2 and the next surface of the base body 3 is 40 µm in this example.

FIG. 5 shows a flow diagram with which the sequence of a method for producing a solid dosage form is described. With this method, for example, a dosage form according to one of the embodiments shown in FIGS. 1 to 4 can be produced. Below, by way of example, the production of a dosage form as shown in FIG. 4, with a QR code as shown in FIG. 1, is described. The production method is carried out in this case by means of a screen printer. The person skilled in the art understands that, in addition to the steps stated below, further steps may be required, such as, for example, drying or curing steps.

In a first step S1, a first printing paste is provided, which comprises the active ingredient acetylsalicylic acid. In a second step S2, the first printing paste is applied by means of a first printing screen. In this case, the first printing paste can first be applied in a planar manner. By repeating steps S1 and S2, several layers can be formed from the first printing paste on top of one another.

In a third step S3, a second printing paste is provided, which contains a black food colouring agent. In a fourth step S4, the second printing paste is applied by means of a second printing screen. The second printing screen in this case predefines a specific structure, so that the second printing paste is printed in the form of a QR code, as shown in FIG. 1. Subsequently, the first printing paste is applied again, wherein the gaps of the existing layer are first filled by using a corresponding screen. Subsequently, the first printing paste is applied in a planar manner.

The invention claimed is:

1. A solid dosage form for active ingredient release, the solid dosage form contained in a tablet comprising:
   a three-dimensional base body, wherein the three-dimensional base body comprises an active ingredient, and
   a portion having a structure forming a two-dimensional identifier,
   wherein the portion is integral with the three-dimensional base body.

2. The solid dosage form according to claim 1, wherein the portion is produced by means of screen printing.

3. The solid dosage form according to claim 1, wherein the three-dimensional base body is produced by means of screen printing.

4. The solid dosage form according to claim 1, wherein the solid dosage form is produced by means of screen printing.

5. The solid dosage form according to claim 1, wherein the two-dimensional identifier is a barcode, a QR code or a haptic code.

6. The solid dosage form according to claim 1, wherein the two-dimensional identifier has a resolution of 50 to 500 dpi.

7. The solid dosage form according to claim 1, wherein the two-dimensional identifier has at least a point or a line with a thickness between 20 µm and 700 µm.

8. The solid dosage form according to claim 1, wherein also the portion contains the active ingredient.

9. The solid dosage form according to claim 8, in particular wherein an active ingredient distribution runs continuously through the solid dosage form over the three-dimensional base body and the portion.

10. The solid dosage form according to claim 1, wherein the portion contains a colouring agent.

11. The solid dosage form according to claim 1, wherein the structure has a three-dimensional extension, wherein the three-dimensional extension of the structure includes a two-dimensional identifier formed along a first dimension and a second dimension of the three-dimensional extension, and wherein the three-dimensional extension of the structure has a thickness of 2 µm to 1000 µm along a third dimension of the three-dimensional extension.

12. The solid dosage form according to claim 1, wherein the portion is present at a surface of the solid dosage form.

13. The solid dosage form according to claim 12, wherein an outwardly directed surface of the portion is planar with a surface of the three-dimensional base body.

14. The solid dosage form according to claim 12, wherein the surface of the solid dosage form is smooth and stepless in a region of the portion.

15. The solid dosage form according to claim 1, wherein the portion is not present at a surface of the solid dosage form.

16. The solid dosage form according to claim 15, wherein a distance of the portion to a surface of the three-dimensional base body is in a range of 2 µm to 1000 µm.

17. The solid dosage form according to claim 1, wherein the portion is not designed as haptically perceptible relief or counter-relief.

18. The solid dosage form according to claim 1, wherein the solid dosage form is designed as tablet, and wherein the active ingredient is a pharmaceutical active ingredient.

19. The solid dosage form according to claim 1, wherein the portion comprises a marker which is detectable after administration of the solid dosage form, wherein the marker is preferably detectable by means of an imaging method.

20. A method for production by means of screen printing of a dosage form, the method comprising:
   providing a first printing paste comprising an active ingredient;
   applying the first printing paste by means of a first printing screen;
   providing a second printing paste comprising a colouring agent; and
   applying the second printing paste by means of a second printing screen to form a portion of the dosage form, wherein the portion has a structure forming a two-dimensional identifier of the dosage form,
   wherein a pattern of the second printing screen defines a structure of the portion.

* * * * *